United States Patent [19]

Kochansky et al.

[11] Patent Number: 4,464,390

[45] Date of Patent: Aug. 7, 1984

[54] CONTROL OF PARASITIC MITES WITH ALKYL CARBAMATES

[75] Inventors: Jan Kochansky, Adelphi, Md.; Fred C. Wright, Kerrville, Tex.

[73] Assignee: The United States of America as represented by the Secretary of Agriculture, Washington, D.C.

[21] Appl. No.: 443,995

[22] Filed: Nov. 23, 1982

[51] Int. Cl.³ ............................................. A01N 47/10
[52] U.S. Cl. ................................................... 424/300
[58] Field of Search ........................................ 424/300

[56] References Cited

U.S. PATENT DOCUMENTS

| | | | |
|---|---|---|---|
| 3,852,416 | 12/1974 | Grubb et al. | 424/14 |
| 3,950,374 | 4/1976 | Ueda et al. | 260/453 R |
| 3,958,006 | 5/1976 | Payne | 424/300 |
| 3,962,457 | 6/1976 | Wakamori et al. | 424/300 |

FOREIGN PATENT DOCUMENTS 0042228  5/1981  European Pat. Off. .

Primary Examiner—Leonard Schenkman
Attorney, Agent, or Firm—M. Howard Silverstein; William E. Scott; David G. McConnell

[57] ABSTRACT

Certain aliphatic carbamates and thiocarbamates are useful in controlling scabies mites and other parasitic mites.

7 Claims, No Drawings

CONTROL OF PARASITIC MITES WITH ALKYL CARBAMATES

BACKGROUND OF THE INVENTION

1. Field of The Invention

This invention relates to the control of scabies mites and other parasitic mites and more specifically to the control of these parasites with certain aliphatic carbamates and thiocarbamates.

2. Description of The Art

A particular shortcoming in the control of scabies mites in livestock is the fact that at present there are only four chemicals registered with the Environmental Protection Agency for use in the United States as dips on cattle and sheep and approved by the Animal and Plant Health Inspection Service, U.S. Department of Agriculture, for quarantine purposes. Although the four chemicals are effective in the control of scabies, their use presents certain disadvantages. Three of the chemicals, toxaphene, coumaphos, and phosmet, cannot be used on lactating dairy cattle, and beef cattle treated with phosmet and toxaphene must be held 21 and 28 days, respectively, before slaughter to avoid pesticide residue problems. In fact, toxaphene, one of the most widely used agricultural insecticides in the world, has been found by the National Cancer Institute to cause liver cancer in male and female mice. The fourth chemical, lime-sulfur, which is used on lactating dairy cattle, must be heated to 95° to 105° F. to be effective.

SUMMARY OF THE INVENTION

An object of this invention is to provide new chemicals useful in the control of scabies mites and other parasitic mites.

Another object is to provide compounds that are lethal to scabies mites and other parasitic mites yet have relatively low vertebrate toxicities so that they are not toxic or harmful to the host.

A further object is to provide compounds that are lethal to scabies mites and other parasitic mites at concentrations equivalent to or far below those required for most of the currently used chemicals.

A still further object is to provide compounds that are economical to use for the control of scabies mites and other parasitic mites.

In general, according to this invention, certain aliphatic straight and branched chain esters of N-alkyl carbamic and thiocarbamic acids having a total of from 6 to 24 carbon atoms are found to be highly effective for controlling scabies mites and other parasitic mites. Compounds found useful for the purpose of this invention are represented by the general formula $$\mathrm{RXCNHR'} \quad \overset{X'}{\underset{\|}{}}$$

wherein each of R and R' is a straight or branched chain alkyl group of from one to twenty carbon atoms and wherein the total number of carbon atoms in R and R' combined is from six to twenty-four and X and X' are individually oxygen or sulfur.

More specifically, the general formula embodies the following types of compounds that have been found useful for the purposes of this invention

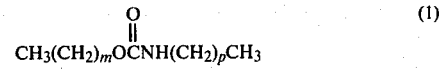

wherein the total of the integers m and p is from 6 to 16;

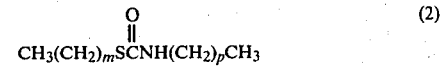

wherein the total of the integers m and p is from 5 to 15;

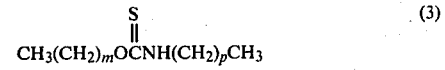

wherein the total of the integers m and p is from 5 to 16;

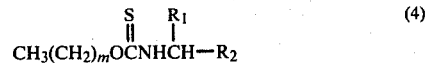

in which m is an integer from 5 to 14 $R_1$ and $R_2$ are lower alkyl groups of from 1 to 4 carbon atoms. In addition, compounds having the structures of types 1 to 3 in which one or both alkyl groups are branched chain are also useful for the purposes of this invention. Examples of this type are 3,7-dimethyloctyl and 2-ethylehexyl.

DESCRIPTION OF THE INVENTION

In 1975, parasitic mites caused an estimated $157 million loss to the U.S. livestock industry. Even though there were only 45 confirmed outbreaks of cattle scabies in the United States in 1975, approximately $65 million of the loss was due to psoroptic scabies in cattle. The problem has since increased in severity and in 1978 alone over 300 outbreaks of psoroptic scabies were confirmed in the United States.

Virtually all mammals including man suffer from parasitic mites and domestic animals, particularly livestock, are no exception. Psoroptic scabies of cattle is a universal problem; infestations have been and are today reported from all areas of the world. In recent years, following a violent outbreak in 1971, common scabies has become an ever increasing threat to the cattle industry and to animal health agencies in the United States. Consequently, in the United States, this disease must be reported to and is quarantined by the Veterinary Services of the Animal and Plant Health Inspection Services of the U.S. Department of Agriculture. With the distinct possibility that the use of certain of the more effective of the chemicals used for scabies mites control may be banned in the future, the need for new chemicals for control of scabies mites is even more urgent and critical.

The difficulty in finding safe active chemicals is partially responsible for the low number of registered compounds for control of scabies mites. Out of thousands of compounds tested in both government and industry evaluation programs, relatively few have been found to be both safe and effective against scabies mites and other parasitic mites. Consequently, it was very surprising and quite unexpected when we found that a number of N-substituted aliphatic carbamate and thiocarbamate esters of this invention displayed very high miticidal activity against scabies mites.

The compounds of this invention are prepared by several methods which are well known to those skilled in the art. Compounds of type 1 may be prepared by the reaction of alcohols with alkyl isocyanates either without catalyst or with the use of basic catalysts such as pyridine, diazabicyclooctane, 4-dimethylaminopyridine, or polymers having tertiary amino groups such as poly(4-vinyl pyridine) or dimethylaminomethyl-substituted poly(styrene-divinylbenzene) resins.

For example, 8.6 g (50 mmol) of 1-undecanol, 5 ml (1.07 eq.) n-propyl isocyanate and 50 ml diethyl ether were heated in a stainless steel bomb at 65° for 72 hours. Solvent and excess isocyanate were removed on a rotary evaporator and the residue was crystallized from hexane to give 11.5 g (89%) of 1-undecyl propylcarbamate, mp 45°-45.5°.

Alternatively, these esters may be prepared by treating alkyl chloroformates with alkyl amines in the presence of triethylamine or other acid acceptor in an inert solvent such as hexane or toluene. To a mixture of 20 ml (100 mmol) decylamine and 10 ml pyridine was added, in two portions, 40 ml of a toluene solution of n-butyl chloroformate (about 100 mmol). The flask was cooled under running water between additions of acid chloride. After the reaction was complete as determined by the lack of any more white precipitate, the slurry was diluted with hexane, washed twice with water, twice with cold dilute HCL, once with water, once with saturated aqueous $NaHCO_3$, and once with brine. After drying with $MgSO_4$, the solvent was removed and the residue was distilled: B.P. 176°-178°/4.5 mm and the product (20.7 g, 80%) was 95% pure by gas chromatography. After crystallization from hexane, the compound melted at 23.5°-25° C.

Thiolcarbamates of type 2 were prepared similarly, either from alkyl mercaptans and isocyanates in the presence of amine catalysts or from alkyl chlorothiolformates and amines in the presence of an acid acceptor.

Thionocarbamates of types 3 and 4 were prepared from alkyl isothiocyanates and alcohols in the presence of basic catalysts such as pyridine or 4-dimethylaminopyridine. Boron trifluoride promoted this reaction, but also promoted the rearrangement of the thionocarbamate product to thiolcarbamates of type 2, so only basic catalysts were used. Since isothiocyanates are much less reactive than isocyanates, more catalyst and a higher temperature had to be used. For example, 100 mmol of 1-undecanol, 2 ml of pyridine, 100 mmol of n-butyl isothiocyanate and 50 ml of ether were heated in a stainless steel bomb at 120° C. for 3 days. The crude product was distilled to a vapor temperature of 90°/1 mm to remove unreacted isothiocyanate, then the residue was chromatographed on 250 g silica gel. Two 500 ml fractions of hexane and a 500 ml fraction of 2.5% ether/hexane gave only traces of colorless oils. The product was eluted with 500 ml of 5% ether/hexane followed by 500 ml of 10% ether/hexane. Later franctions of 10% and 25% ether/hexane gave material contaminated with starting alcohol. Combined yield of pure material, as determined by thin layer chromatography, was 15.6 g (55%) of an orange oil.

Spectrometric examination (IR, NMR, M.S.) of representative compounds confirmed the identity of the products.

The compounds were tested in vitro on the rabbit ear mite, *Psoroptes cuniculi*, which has come to be used as the model biological system for testing candidate chemicals for miticidal activity against scabies mites such as the common scabies mite of cattle and sheep, *Psoroptes ovis*, and other parasitic mites. Groups of large mites (20 to 25 adults and nymphs) were exposed to the chemicals using a modification of the "tea bag" technique (J. Econ. Entomol. 65, 174, 1972; Southwestern Entomol. 4, 40, 1979), by dipping them for 30 seconds in aqueous emulsions prepared from an emulsifiable concentrate of the test chemical. In a few early tests, a 10% emulsifiable concentrate containing 10% test chemical, 85% ethanol or acetone and 5% Triton X-100 was used. In later tests, a 25% emulsifiable concentrate containing 25% test chemical, 65% xylene, and 10% Triton X-100 was used. Triton X-100 is octylphenoxy polyethoxy ethanol, a nonionic surfactant containing an average of 8.5 ethylene oxide groups. Other emulsifiers and solvents known to those skilled in the art are equally suitable. Each compound was tested at a range of concentrations. At 24 hours after dipping, the mites were examined with the aid of a dissecting microscope, and those mites that showed absolutely no movement or that were able to move their legs but were unable to walk were judged as dead. Under these test conditions the range of concentrations required to kill 100% of the mites with three commercial miticide formulations used for scabies control, coumaphos, phosmet and toxaphene, are >0.1%, 0.005-0.01% and 0.00005-0.0001%, respectively.

Table I shows the activity observed on testing compounds of type 1 against *P. cuniculi*. Only a few compounds are lethal at or near 0.001%, and these are represented by those compounds in which the carbon chain length of R plus R' is from 10 to 14.

Table II shows the activity of compounds of type 2. The most active of these compounds are no more active than those of type 1, but activity is more uniform, with 11 compounds lethal at 0.001%. In these compounds the carbon chain length of R plus R' is from 11 to 13. In those compounds lethal at ≦0.01% the carbon chain length of R plus R' is from 8 to 14.

Activity of the thionocarbamates, type 3, Table III, is even more broadly distributed. Thirty-five of 62 compounds with straight-chain alkyl groups were lethal at 0.001% or less, with most of the rest lethal at 0.01%. In those lethal at 0.001% the carbon chain length of R plus R' is from 10 to 16. Three of the N-isopropyl (type 4) compounds were also lethal at 0.001% is contrast to the thiolcarbamate series where N-isopropyl esters were inactive.

Of those compounds where R was a branched alkyl group (Table IV), only the 3,7-dimethyloctyl thionocarbamates were active at 0.001%.

Various analogous compounds were tested and found inactive or much less active. Decyl methyl carbonate and octyl and decyl butyl carbonates were inactive at 0.1% as were decyl O-methyl and O-butyl xanthates. Decyl N-methyl- and N-butyl-dithiocarbmates were active at 0.01%, as was N-decyl N'-butyl thiourea, while decylmethylurea, decylethylthiourea and decylpropylthiourea were active only at 0.1% or more.

Unsubstituted carbamates $ROCONH_2$, where R is n-octyl, n-decyl, or n-dodecyl, were inactive at 0.1%, showing that an N-alkyl substituent is necessary for activity.

N,N-dialkyl carbamates were inactive at 0.1%. Compounds tested included decyldiethylcarbamate, dodecyldimethyl through dodecyl di-n-hexyl carbamates, dodecyl tetramethylene, pentamethylene and hexamethylene carbamates. S-decyl-N,N-dialkyl thiocarbamates where alkyl is methyl through butyl were also inactive at 0.1%.

Substitution of oxygen atoms for one or more of the methylene groups in the ester chain destroyed activity. $CH_3(OCH_2CH_2)_3OCONHBu$, $Bu(OCH_2CH_2)_2OCONHCOCONHBu$, and $CH_3(CH_2)_5OCH_2CH_2CH_2OCONHMe$ were inactive at 0.1%, but replacement of only one methylene group with sulfur gave moderately active compounds. $CH_3(CH_2)_5S(CH_2)_3OCONHCH_3$, $CH_3(CH_2)_6SCH_2CH_2OCONHCH_3$, and —OCONHBu were active at 0.01%.

Table V summarizes the structures of all compounds active at 0.001%.

Four of the compounds active against *P. cuniculi* were also tested against *Psoroptes ovix* the common scabies mite of cattle and sheep. Decyl methyl, decyl ethyl, and decyl butyl carbamate were lethal to both species at 0.005%. Decyl propyl carbamate was lethal to *P. cuniculi* at 0.001% but required 0.005% to kill *P. ovis*.

Four compounds were tested in vivo at a range of concentrations for miticidal activity against scabies mites and other parasitic mites using rabbits infested in both ears with the rabbit ear mite *Psoroptes cuniculi*. Both ears of each infested rabbit were treated with aqueous emulsions containing from 0.25% to 1.0% of the test compound prepared from a 25% emulsifiable concentrate of the test compound, which was diluted to the test concentration with water.

A 25 ml volume used for each rabbit, 12.5 ml in each ear. All rabbits wore plastic collars to restrict grooming. Prior to treatment, the infestation in each ear was rated and then some of the very heavy scab removed. Each ear was filled with test solution, held and massaged for at least one minute. The outside of the ears and area around the head and neck was swabbed with the test solution. One rabbit was treated with each test solution and one rabbit was treated with the solvent blank at comparable dilutions. The rabbits were examined weekly with an otoscope for 6 weeks posttreatment and then the ears were swabbed with "Q"-tips to check for live mites.

The infection rating system used is as follows: 0.5=trace of irritation; $1 = <\frac{1}{8}$ of ear involved; $2=\frac{1}{8}$ of ear; $3=\frac{1}{4}$ of ear; $4=\frac{1}{2}$ of ear; $5=\frac{3}{4}$ of ear; $6=$full ear; and $7=$full ear with spill over on to head or body of rabbit.

The activity of the compounds themselves is classified as follows:

A = No reduction in number of mites or amount of scab,
B = Initial reduction in number of mites or scab but mite population soon builds back up,
C = Neat complete elimination of mites and scab; mites not found until end of test,
D = Complete elimination of mites and scabs.

The results of these in vivo tests are shown in Table VI.

Compounds 4 and 16 from Table V were tested on cattle infested with *Psoroptes ovis* as follows:

The evaluation method was as follows: eleven Hereford heifers moderately to severely infested with *P. ovis* were used. All were of similar age and size and were accustomed to being restrained in anti-grooming stanchions. Each animal in turn was removed from its stanchion, placed in a stanchion in the spray room, and carefully sprayed with two gallons of the appropriate spray by means of an electric sprayer. The animals were sprayed with the compounds as shown in Table VII. The toxaphene was a commercial formulation (Cooper-Tox Livestock—61% emulsifiable concentrate). Compounds 4 and 16 were formulated as 25% emulsifiable concentrates. The animals were returned to clean stanchions after spraying and remained in these throughout the study. A scraping from each side, about 1 sq. in. in size, was taken from each animal before treatment and at predetermined time intervals after treatment. The number of live mites in each sample was recorded. The total number of live mites in the scrapings is shown in Table VII. Applying the compounds by spraying them is not the most effective way to evaluate their efficacy; dipping the animals is more effective but requires much more material. Even the standard, toxaphene, did not reliably eliminate all infestation from these animals. It is apparent, however, that compounds 4 and 16 are approximately as effective as toxaphene against actual infestations of common cattle scabies.

TABLE I

Minimum concentrations (%) of alkyl N—alkyl carbamates required to kill 100% of nymphs and/or adults of the rabbit ear mite *(Psoroptes cuniculi)* exposed for 30 seconds in "tea bag" dipping tests.

Compound ROC(O)NHR'

| R' | 1 | 2 | 3 | 4 | 5 | 6 | 7 | 8 | 9 | 10 | 11 | 12 |
|---|---|---|---|---|---|---|---|---|---|---|---|---|
| R 1 | | | | | | | | >0.1 | | 0.005 | | >0.1 |
| 2 | | | | | | | | >0.1 | | >0.1 | | 0.1 |
| 3 | | | | | | | | | | | | |
| 4 | | | | | >0.1 | >0.1 | >0.1 | 0.01 | 0.01 | 0.01 | 0.01 | |
| 5 | | | | | | | | | | | | |
| 6 | >0.1 | | >0.1 | >0.1 | | | | | | | | |
| 7 | >0.1 | | >0.1 | >0.1 | 0.01 | 0.01 | 0.001 | | | >0.1 | | |
| 8 | 0.05 | >0.1 | 0.01 | 0.005 | | | | | | | | |
| 9 | >0.1 | >0.1 | 0.1 | 0.01 | | | | | | | | |
| 10 | 0.005 | 0.005 | 0.001 | 0.0005 | 0.01 | >0.1 | | >0.1 | | | | |
| 11 | 0.1 | 0.01 | 0.01 | >0.1 | | | | | | | | |
| 12 | >0.1 | >0.1 | >0.1 | >0.1 | | | | | | | | |
| 13 | | | | | | | | | | | | |
| 14 | >0.1 | >0.1 | >0.1 | >0.1 | | | | | | | | |

TABLE II

Minimum concentrations (%) of S—alkyl N—alkyl thiocarbamates required to kill 100% of nymphs and/or adults of the rabbit ear mite (*Psoroptes cuniculi*) exposed for 30 seconds in "tea bag" dipping tests.

Compound RSC(O)NHR'

| R \ R' | 1 | 2 | 3* | 4 | 5 | 6 | 7 | 8 | 9 | 10 | 11 | 12 |
|---|---|---|---|---|---|---|---|---|---|---|---|---|
| 1 | >0.1 | >0.1 | >0.1 | >0.1 | >0.1 | >0.1 |  | 0.01 |  | >0.1 |  | >0.1 |
| 2 | >0.1 |  | >0.1 | >0.1 | >0.1 | >0.1 | >0.1 | 0.01 | 0.01 | 0.01 |  | >0.1 |
| 3 | >0.1 | >0.1 | >0.1 | >0.1 | >0.1 | 0.01 | 0.01 | 0.01 | 0.001 | 0.01 |  |  |
| 4 |  | >0.1 | >0.1 | >0.1 | >0.1 | 0.01 | 0.01 | 0.001 | 0.001 | >0.1 |  |  |
| 5 | >0.1 | >0.1 | >0.1 | >0.1 | >0.1 | 0.01 | 0.001 | 0.001 |  |  |  |  |
| 6 | 0.1 | >0.1 | >0.1 | >0.1 | >0.01 | 0.001 | 0.001 | 0.01 |  |  |  |  |
| 7 | 0.01 | 0.01 | 0.01 | 0.01 | >0.01 | >0.1 | >0.1 | >0.1 |  |  |  |  |
| 8 | 0.01 | 0.01 | 0.01 | 0.001 | >0.1 | >0.1 |  |  |  |  |  |  |
| 9 | 0.01 | 0.001 | 0.001 | 0.01 |  |  |  |  |  |  |  |  |
| 10 | 0.001 | 0.01 | 0.1 | >0.1 |  |  |  |  |  |  |  |  |
| 11 | 0.1 | >0.1 | >0.1 | >0.1 |  |  |  |  |  |  |  |  |
| 12 | >0.1 | >0.1 | >0.1 | >0.1 |  |  |  |  |  |  |  |  |
| 13 |  |  |  |  |  |  |  |  |  |  |  |  |
| 14 | >0.1 |  |  |  |  |  |  |  |  |  |  |  |

* $C_7-C_{11}$ SCONHCH(CH$_3$)$_2$ all >0.1

TABLE III

Minimum concentrations (%) of O—alkyl N—alkyl thiocarbamates required to kill 100% of nymphs and/or adults of the rabbit ear mite (*Psoroptes cuniculi*) exposed for 30 seconds in "tea bag" dipping tests.

Compound ROC(S)NHR'

| R \ R' | 1 | 2 | 3 | 4 | 5 | 6 | 7 | 8 | 9 | 10 | 11 | 12 | iso-C$_3$ |
|---|---|---|---|---|---|---|---|---|---|---|---|---|---|
| 1 |  |  |  |  |  |  |  | 0.01 |  | 0.001 |  | 0.001 |  |
| 2 |  |  |  |  |  |  |  | 0.01 |  | 0.001 |  | 0.001 |  |
| 3 |  |  |  |  |  |  |  | 0.1 |  | 0.001 |  | 0.001 |  |
| 4 |  |  |  |  |  |  |  | 0.001 |  | 0.001 |  | 0.001 |  |
| 5 |  |  |  |  |  |  |  | 0.001 |  | 0.001 |  | >0.1 |  |
| 6 |  |  |  |  |  | 0.001 |  | 0.001 |  | 0.01 |  | 0.01 |  |
| 7 |  |  |  | 0.01 |  |  |  |  |  |  |  |  |  |
| 8 | 0.01 | 0.01 | 0.01 | 0.001 | 0.001 | 0.001 |  | 0.001 |  |  |  |  | 0.1 |
| 9 | 0.001 | 0.01 | 0.01 | 0.001 | 0.001 | 0.001 |  |  |  |  |  |  | 0.01 |
| 10 | 0.0005 | 0.01 | 0.01 | 0.001 | 0.001 | 0.01 | >0.1 |  |  |  |  |  | 0.001 |
| 11 | 0.001 | 0.001 | 0.001 | 0.001 | 0.01 |  |  |  |  |  |  |  | 0.001 |
| 12 | 0.001 | 0.001 | 0.001 | 0.001 |  | >0.1 |  |  |  |  |  |  | 0.01 |
| 13 | 0.001 | 0.001 | 0.01 | 0.01 |  |  |  |  |  |  |  |  | 0.001 |
| 14 | 0.001 | 0.01 |  | >0.1 |  |  |  |  |  |  |  |  | >0.1 |
| 15 | >0.1 |  |  |  |  |  |  |  |  |  |  |  |  |
| 16 | >0.1 |  |  |  |  |  |  |  |  |  |  |  |  |

TABLE IV

Minimum concentrations of some branched alkyl carbamates required to kill 100% of tested *Ps. cuniculi*.

| RX$_2$CNHR' | R' = CH$_3$ | C$_2$H$_5$ | C$_3$H$_7$ | C$_4$H$_9$ | C$_5$H$_{11}$ |
|---|---|---|---|---|---|
| (branched)OCONH | >0.1 |  |  |  |  |
| (branched)SCONH | 0.01 |  |  | 0.01 |  |
| (branched)OC(S)NH | 0.001 |  | 0.001 | 0.001 |  |
| 2-ethylhexylOCONH(2EH) | >0.1 | >0.1 | >0.1 | >0.1 | 0.01 |
| 2EHOC(S)NH | 0.01 | 0.01 | 0.01 | 0.01 |  |
| (branched)OCONH | 0.1 |  |  |  |  |

TABLE V

Carbamates of all types lethal to *P. cuniculi* at 0.001% or less

| Compound No. | Structure |
|---|---|
| 1 | $CH_3(CH_2)_9OCONHCH_2CH_2CH_3$ |
| 2 | $CH_3(CH_2)_9OCONH(CH_2)_3CH_3$ |
| 3 | $CH_3(CH_2)_6OCONH(CH_2)_6CH_3$ |
| 4 | $CH_3(CH_2)_9SC(O)NHCH_3$ |
| 5 | $CH_3(CH_2)_8SC(O)NHCH_2CH_3$ |
| 6 | $CH_3(CH_2)_8SC(O)NH(CH_2)_2CH_3$ |
| 7 | $CH_3(CH_2)_7SC(O)NH(CH_2)_3CH_3$ |
| 8 | $CH_3(CH_2)_5SC(O)NH(CH_2)_5CH_3$ |
| 9 | $CH_3(CH_2)_5SC(O)NH(CH_2)_6CH_3$ |
| 10 | $CH_3(CH_2)_4SC(O)NH(CH_2)_6CH_3$ |
| 11 | $CH_3(CH_2)_4SC(O)NH(CH_2)_7CH_3$ |
| 12 | $CH_3(CH_2)_3SC(O)NH(CH_2)_7CH_3$ |
| 13 | $CH_3(CH_2)_3SC(O)NH(CH_2)_8CH_3$ |
| 14 | $CH_3(CH_2)_2SC(O)NH(CH_2)_8CH_3$ |
| 15 | $CH_3(CH_2)_8OC(S)NHCH_3$ |
| 16 | $CH_3(CH_2)_9OC(S)NHCH_3$ |
| 17 | $CH_3(CH_2)_{10}OC(S)NHCH_3$ |
| 18 | $CH_3(CH_2)_{11}OC(S)NHCH_3$ |
| 19 | $CH_3(CH_2)_{12}OC(S)NHCH_3$ |
| 20 | $CH_3(CH_2)_{13}OC(S)NHCH_3$ |
| 21 | $CH_3(CH_2)_{10}OC(S)NHCH_2CH_3$ |
| 22 | $CH_3(CH_2)_{11}OC(S)NHCH_2CH_3$ |
| 23 | $CH_3(CH_2)_{12}OC(S)NHCH_2CH_3$ |
| 24 | $CH_3(CH_2)_{10}OC(S)NH(CH_2)_2CH_3$ |
| 25 | $CH_3(CH_2)_{11}OC(S)NH(CH_2)_2CH_3$ |
| 26 | $CH_3(CH_2)_7OC(S)NH(CH_2)_3CH_3$ |
| 27 | $CH_3(CH_2)_8OC(S)NH(CH_2)_3CH_3$ |
| 28 | $CH_3(CH_2)_9OC(S)NH(CH_2)_3CH_3$ |
| 29 | $CH_3(CH_2)_{10}OC(S)NH(CH_2)_3CH_3$ |
| 30 | $CH_3(CH_2)_{11}OC(S)NH(CH_2)_3CH_3$ |
| 31 | $CH_3(CH_2)_7OC(S)NH(CH_2)_4CH_3$ |
| 32 | $CH_3(CH_2)_8OC(S)NH(CH_2)_4CH_3$ |
| 33 | $CH_3(CH_2)_9OC(S)NH(CH_2)_4CH_3$ |
| 34 | $CH_3(CH_2)_5OC(S)NH(CH_2)_5CH_3$ |
| 35 | $CH_3(CH_2)_7OC(S)NH(CH_2)_5CH_3$ |
| 36 | $CH_3(CH_2)_8OC(S)NH(CH_2)_5CH_3$ |
| 37 | $CH_3(CH_2)_3OC(S)NH(CH_2)_7CH_3$ |
| 38 | $CH_3(CH_2)_4OC(S)NH(CH_2)_7CH_3$ |
| 39 | $CH_3(CH_2)_5OC(S)NH(CH_2)_7CH_3$ |
| 40 | $CH_3(CH_2)_7OC(S)NH(CH_2)_7CH_3$ |
| 41 | $CH_3OC(S)NH(CH_2)_9CH_3$ |
| 42 | $CH_3CH_2OC(S)NH(CH_2)_9CH_3$ |
| 43 | $CH_3(CH_2)_2OC(S)NH(CH_2)_9CH_3$ |
| 44 | $CH_3(CH_2)_3OC(S)NH(CH_2)_9CH_3$ |
| 45 | $CH_3(CH_2)_4OC(S)NH(CH_2)_9CH_3$ |
| 46 | $CH_3OC(S)NH(CH_2)_{11}CH_3$ |
| 47 | $Ch_3CH_2OC(S)NH(CH_2)_{11}CH_3$ |
| 48 | $CH_3(CH_2)_2OC(S)NH(CH_2)_{11}CH_3$ |
| 49 | $CH_3(CH_2)_3OC(S)NH(CH_2)_{11}CH_3$ |
| 50 | $CH_3(CH_2)_9OC(S)NHCH(CH_3)_2$ |
| 51 | $CH_3(CH_2)_{10}OC(S)NHCH(CH_3)_2$ |
| 52 | $CH_3(CH_2)_{12}OC(S)NHCH(CH_3)_2$ |
| 53 | $(CH_3)_2CH(CH_2)_2CH(CH_3)(CH_2)_2OC(S)NHCH_3$ |
| 54 | $(CH_3)_2CH(CH_2)_2CH(CH_3)(CH_2)_2OC(S)NH(CH_2)_2CH_3$ |
| 55 | $(CH_3)_2CH(CH_2)_2CH(CH_3)(CH_2)_2OC(S)NH(CH_2)_2CH_3$ |

TABLE VI

Effects of alkyl carbamates on elimination of mites and scab from the ears of rabbits infested with rabbit ear mites (*Psoroptes cuniculi*).

| Compound No. (see Table V) | Concentration | Rating Initial | Rating Final | Classification |
|---|---|---|---|---|
| 1 | 1% | 3.5/2 | * | — |
| 2 | 1% | 3/4 | 0.5/0.5 | D |
| 4 | 1% | 4.5/3.5 | 0.5/0 | D |
| 16 | 1% | 6/4 | 0/0 | D |
| blank | 1% equivalent | 2/1 | 1.5/1.5 | B |
| 1 | 0.5% | 2.5/2.5 | 0/0 | D |
| 2 | 0.5% | 4/4.5 | 4/3.5 | B |
| 4 | 0.5% | 4.5/3 | 0/0 | D |
| 16 | 0.5% | 3/3 | 0/0 | D |
| blank | 0.5% equiv. | 4/5 | 4.5/2 | B |
| 1 | 0.25% | 2.5/3 | 1/3.5 | B |
| 4 | 0.25% | 4/3.5 | 0/0 | D |
| 16 | 0.25% | 5/3 | 6/3 | B |

* rabbit died of unknown causes after three weeks.

TABLE VII

Comparison of Toxaphene and alkyl carbamates in Spray Trials Against *Psoroptes ovis* of cattle[a].

| Treatment and Concentration(%) | No. of live mites in scrapings[b] at days posttreatment | | | | | | | |
|---|---|---|---|---|---|---|---|---|
| | 0 | 3 | 10 | 17 | 24 | 31 | 38 | 45 |
| Toxaphene - 0.5 | 264 | 0 | 3 | 402[c] | | 4 | 4 | 88[c] |
| " | 1423 | 0 | 0 | 0 | | 0 | 0 | 0 | 0 |
| " | 110 | 0 | 0 | 0 | | 0 | 0 | 0 | 0 |
| Compound 4-1.0 | 61 | 0 | 0 | 0 | | 0 | 0 | 0 | 32 |
| " | 1882 | 0 | 0 | 0 | 698[c] | | | 894[c] | |
| Compound 4-0.5 | 1001 | | 0 | 0 | 16 | 20 | 0 | |
| " | 149 | | 0 | 0 | 0 | 0 | 0 | 71 |
| Compound 16-1.0 | 53 | 2 | 0 | 1 | 70[c] | | | | |
| " | 27 | 0 | 1 | 0 | | 4 | 0 | 3 |
| Compound 16-0.5 | 33 | 0 | 0 | 0 | 0 | 5 | 0 | 0 |
| " | 374 | 0 | 0 | 0 | 0 | 29 | 33[c] | |

[a]Each animal was sprayed with 2 gal. of appropriate concentration.
[b]Total number of live mites found in 2 scrapings (one from each side of animal). Each scraping was 1 sq. inch in size.
[c]Compound classed as failure due to thriving population of *P. ovis*; animal removed from test.

We claim:

1. A method of controlling scabies mites and other parasitic mites comprising applying to said mites a miticidally effective amount of a compound of the formula, $$RXCNHR'$$
$$\overset{X'}{\underset{\|}{}}$$

wherein each of R and R' is a straight or branched chain alkyl group having from one to twenty carbon atoms and wherein the total number of carbon atoms in R and R' combined is from six to twenty-four, and X and X' are individually oxygen or sulfur.

2. The method of claim 1 in which the compound has the formula $$CH_3(CH_2)_mOCNH(CH_2)_pCH_3$$
(with O double-bonded to C)

wherein each of m and p is an integer from 0 to 19 and the total of m and p is from 4 to 22.

3. The method of claim 1 in which the compound has the formula $$CH_3(CH_2)_mSCNH(CH_2)_pCH_3$$
(with O double-bonded to C)

wherein each of m and p is an integer from 0 to 19 and the total of m and p is from 4 to 22.

4. The method of claim 1 in which the compound has the formula $$CH_3(CH_2)_mOCNH(CH_2)_pCH_3$$
(with O double-bonded to C)

wherein each of m and p is an integer from 0 to 19 and the total of m and p is from 4 to 22.

5. The method of claim 1 in which the compound has the formula $$CH_3(CH_2)_mOCNHCH{-}R_2$$
(with S double-bonded to C, and $R_1$ on the CH)

wherein m is an integer from 5 to 14 and each of $R_1$ and $R_2$ is lower alkyl group having from 1 to 4 carbon atoms.

6. The method of claim 1 in which the compound has the formula $$CH_3CH(CH_2)_mCH(CH_2)_pXCNHR'$$
(with $R_3$ on first CH, $R_4$ on second CH, and X' double-bonded to C)

wherein each of $R_3$ and $R_4$ is lower alkyl, each of m and p is an integer from one to three, X and X' are individually oxygen or sulfur and R' is a primary or secondary alkyl group of from one to ten carbon atoms.

7. A method of controlling scabies mites and other parasitic mites comprising applying to said mites a miticidally effective amount of a compound of the formula $$CH_3(CH_2)_mA(CH_2)_nXCNH(CH_2)_pCH_3$$
(with X' double-bonded to C)

wherein A, X and X' are individually oxygen or sulfur, each of m, n and p is a integer from 0 to 19, and the total m, n and p is from 3 to 21.

* * * * *

UNITED STATES PATENT AND TRADEMARK OFFICE
CERTIFICATE OF CORRECTION

PATENT NO. : 4,464,390
DATED : August 7, 1984
INVENTOR(S) : Jan Kochansky and Fred C. Wright It is certified that error appears in the above-identified patent and that said Letters Patent is hereby corrected as shown below:

In the specification, Column 5, Line 18, the word "ovix" should read -ovis-.

In the claims:
  In Claim 4, Column 11, Lines 24 and 25, the formula should read as follows:

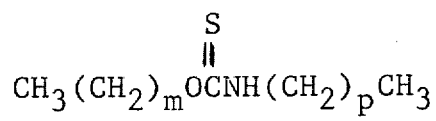

In Claim 6, Column 12, Lines 12 and 13, the formula should read as follows:

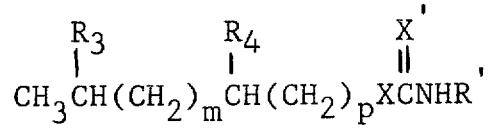

Signed and Sealed this

Twenty-sixth Day of March 1985

[SEAL]

Attest:

DONALD J. QUIGG

Attesting Officer      Acting Commissioner of Patents and Trademarks